(12) United States Patent
Di Gerolamo et al.

(10) Patent No.: US 7,339,086 B2
(45) Date of Patent: Mar. 4, 2008

(54) PROCESS FOR THE HYDROGENATION OF BRANCHED OLEFINS DERIVING FROM THE DIMERIZATION OF ISOBUTENE

(75) Inventors: Marco Di Gerolamo, San Donato Milanese (IT); Roberto Catani, Milan (IT); Mario Marchionna, Milan (IT)

(73) Assignee: SNAMPROGETTI S.p.A., San Donato Milanese (IT)

( * ) Notice: Subject to any disclaimer, the term of this patent is extended or adjusted under 35 U.S.C. 154(b) by 437 days.

(21) Appl. No.: 10/265,436

(22) Filed: Oct. 7, 2002

(65) Prior Publication Data

US 2003/0078462 A1    Apr. 24, 2003

(30) Foreign Application Priority Data

Oct. 18, 2001    (IT) .......................... MI2001A2167

(51) Int. Cl.
*C07C 2/00*    (2006.01)
*C07C 2/04*    (2006.01)

(52) U.S. Cl. ........................ 585/510; 585/314; 585/329

(58) Field of Classification Search ................ 585/314, 585/329, 510
See application file for complete search history.

(56) References Cited

U.S. PATENT DOCUMENTS 4,367,356 A    1/1983 Ward ........................... 585/315
4,528,411 A *  7/1985 Hutson, Jr. .................. 585/329
5,482,616 A *  1/1996 Brahma et al. ............. 208/143
5,723,687 A    3/1998 Marchionna et al. ....... 568/697
5,811,608 A *  9/1998 Stine et al. .................. 585/316
6,884,916 B1 * 4/2005 Brown et al. ............... 585/530

FOREIGN PATENT DOCUMENTS

EP    0 994 088 A1    4/2000

OTHER PUBLICATIONS

U.S. Appl. No. 10/745,512, filed Dec. 29, 2003, Catani et al.

\* cited by examiner

*Primary Examiner*—Glenn A. Caldarola
*Assistant Examiner*—In Suk Bullock
(74) *Attorney, Agent, or Firm*—Oblon, Spivak, McClelland, Maier & Neustadt, P.C.

(57) ABSTRACT

A process is described for the hydrogenation of olefinic streams containing sulfurated compounds, obtained starting from hydrocarbon cuts containing isobutene (by means of selective dimerization), characterized by fractionating said streams in one or more distillation columns and hydrogenating separately the two fractions obtained. The stream at the head, with a minimum content of sulfurated compounds, is hydrogenated with conventional catalysts based on nickel or noble metals (Platinum and/or Palladium), extremely active but also very sensitive to sulfur, whereas the bottom of the column, rich in sulfurated compounds, is treated with bimetallic catalysts (for example Ni/Co and/or Ni/Mo), less active but not deactivated by sulfur.

16 Claims, 2 Drawing Sheets

PROCESS FOR THE HYDROGENATION OF BRANCHED OLEFINS DERIVING FROM THE DIMERIZATION OF ISOBUTENE

BACKGROUND OF THE INVENTION

1. Field of the Invention

The present invention relates to a process for the hydrogenation of olefinic streams containing sulfurated compounds, obtained starting from hydrocarbon cuts containing isobutene (by means of selective dimerization), characterized by fractionating said streams in one or more distillation columns and hydrogenating separately the two fractions obtained. The stream at the head, with a minimum content of sulfurated compounds, is hydrogenated with catalysts based on Nickel or noble metals (platinum and/or palladium, etc.), extremely active but also very sensitive to sulfur, whereas the bottom of the column, rich in sulfurated compounds, is treated with bimetallic catalysts (Ni/Co and/or Ni/Mo), less active but not subject to deactivation on the part of sulfurated compounds.

2. Description of the Background

Refineries throughout the world are currently active in producing "Environmental Low Impact Fuels" (characterized by a reduced content of aromatics, olefins, sulfur and a lower volatility), obviously with the aim of minimizing the effect of their production on the functioning of the refinery itself.

MTBE and alkylated products are the most suitable compounds for satisfying future refinery demands; the use of MTBE at the moment, however, is at high risk and alkylated products are rare.

The ban on fuels in California and the continuous attack on MTBE, due to its poor biodegradability and assumed toxicity, have in fact raised doubts as to its use (and also that of other alkyl ethers) in future reformulated fuels. The removal of this ether will create considerable problems for refineries, as MTBE, in addition to its high octane function, also has a diluting action of products harmful to the environment (sulfur, aromatics, benzene, etc.).

Alkylated products are, without doubt, ideal compounds for reformulated fuels as they satisfy all requisites provided by future environmental regulations, combining a high octane number with a low volatility and the practically complete absence of olefins, aromatics and sulfur.

Another positive aspect of alkylation is that it is capable of activating isoparaffinic hydrocarbons, such as isobutane, for example, which binds itself, by reaction in liquid phase catalyzed by strong acids, with olefins (propylene, butene, pentenes and relative mixtures) producing $C_7$-$C_9$ saturated hydrocarbons with a high octane number.

Higher productions of alkylated products, however, with respect to those currently available, would require the construction of large alkylation units as, due to their scarcity, alkylated products do not represent a commodity which is widely available on the market, but a fuel component for captive use in the refineries which produce them.

This is a serious limitation for the wide-scale use of alkylated products as the construction of new units is limited by the incompatibility of the catalysts used in traditional processes (hydrofluoric acid and sulfuric acid) with the new environmental regulations for the catalysts used: processes with hydrofluoric acid due to the dangerous nature of this acid, especially in populated areas, processes with sulfuric acid due to the large production of acid sludge, which is difficult to dispose of, in addition to the highly corrosive power of the catalyst.

Alternative processes with solid acid catalysts are being developed but their commercial applicability must still be demonstrated.

In order to overcome these problems, resort must therefore be made to the ever-increasing use of purely hydrocarbon products, such as those obtained from the selective dimerization of $C_3$ and $C_4$ olefins, which both for their octane characteristics (high Research Octane Number (RON) and high Motor Octane Number (MON)) and also for their boiling point (poor volatility but low final point), are included in the range of compositions of extreme interest for obtaining fuels which are more compatible with current environmental demands.

In refining, oligomerization (often erroneously called polymerization) processes were widely used in the thirties'-forties' for converting low-boiling $C_3$-$C_4$ olefins into so-called "polymer" fuel. Typical olefins which are oligomerized are mainly propylene, which produces ($C_6$) dimers or slightly higher oligomers depending on the process used, and isobutene which mainly produces ($C_8$) dimers but always accompanied by large quantities of higher oligomers ($C_{12}^+$).

This process leads to the production of a fuel with a high octane number (RON about 97) but with a considerable sensitivity due to the purely olefinic characteristic of the product (for a more detailed description of the process see: J. H. Gary, G. E. Handwerk, "Petroleum Refining: Technology and Economics", $3^{rd}$ Ed., M. Dekker, New York, (1994), 250). The olefinic nature of the product forms an evident limit of the process, as the hydrogenation of these mixtures also causes a considerable reduction in the octane characteristics of the product, which consequently becomes less attractive.

If we concentrate on the oligomerization of isobutene, it is known that this reaction is generally carried out with acid catalysts such as phosphoric acid supported on a solid (for example kieselguhr), cationic exchange acid resins, liquid acids such as $H_2SO_4$ or derivatives of sulfonic acids, silico-aluminas, mixed oxides, zeolites, fluorinated or chlorinated aluminas, etc.

The main problem of dimerization, which has limited its industrial development, is the difficulty in controlling the reaction rate; the high activity of all these catalytic species together with the difficulty in controlling the temperature in the reactor, makes it, in fact, extremely difficult to succeed in limiting the addition reactions of isobutene to the growing chains and consequently to obtain a high quality product characterized by a high selectivity to dimers.

In dimerization reactions, in fact, there is the formation of excessive percentages of heavy oligomers such as trimers (selectivity of 15-60%) and tetramers (selectivity of 2-10%) of isobutene. Tetramers are completely outside the fuel fraction as they are too high-boiling and therefore represent a net loss in yield to fuel; as far as trimers are concerned (or their hydrogenated derivatives), their concentration should be significantly decreased as they are characterized by a boiling point (170-180° C.) at the limit of future specifications on the final point of reformulated fuels.

In order to obtain a higher quality product, by reaching higher selectivities (dimer content >80-85% by weight), it is possible to use different solutions which are able to modify the activity of the catalyst, consequently allowing the reaction rate to be controlled.

oxygenated compounds can be used (tertiary alcohol and/or alkyl ether and/or primary alcohol) in a sub-stoichiometric quantity with respect to the isobutene fed in the charge using tubular and/or adiabatic reactors (IT-MI95/A001140 of 01 Jun. 1995, IT-MI97/A001129 of 15 May 1997 and IT-MI99/A001765 of 05 Aug. 1999).

tertiary alcohols can be used (such as terbutyl alcohol) in a sub-stoichiometric quantity with respect to the isobutene fed in the charge using tubular and/or adiabatic reactors (IT-MI94/A001089 of 27 May 1994).

alternatively it is possible to suitably modify the charge, by mixing fresh charge with at least a part of the hydrocarbon stream obtained after the separation of the product, in order to optimize the isobutene content (<20% by weight) and use a linear olefin/isobutene ratio higher than 3. In this case, the use of reactors such as tubular or Boiling Point Reactors, capable of controlling the temperature increase, is fundamental for obtaining high selectivities (IT-MI2000/A001166 of 26 May 2000).

Operating under these conditions, it is therefore possible to favour the dimerization of isobutene or isobutene/n-butene codimerizations, with respect to oligomerization, and avoid the activation of oligomerization-polymerization reactions of linear butenes which are favoured by high temperatures.

The dimerization product is then preferably hydrogenated to give a completely saturated end-product, with a high octane number and low sensitivity. As an example, the following table indicates the octane numbers and relative boiling points of some of the products obtained by the dimerization of isobutene.

| PRODUCT | RON | MON | b.p. (° C.) |
|---|---|---|---|
| Di-isobutylenes | 100 | 89 | 100-105 |
| Iso-octane | 100 | 100 | 99 |
| Tri-isobutylenes | 100 | 89 | 175-185 |
| Hydrogenated tri-isobutylenes | 101 | 102 | 170-180 |

The hydrogenation of olefins is generally effected using two groups of catalysts:
those based on nickel (20-80% by weight);
those based on noble metals (Pt and/or Pd) supported on alumina with a metal content of 0.1-0.6% by weight.

The operating conditions used for both groups are quite similar; in the case of nickel catalysts, resort must be made, however, to a higher hydrogen/olefin ratio as these catalysts have a greater tendency of favouring the cracking of the olefins. Catalysts based on nickel are obviously less expensive but they are easily poisoned in the presence of sulfurated compounds; the maximum quantity of sulfur they can tolerate is 1 ppm with respect to the 10 ppm approximately, tolerated by catalysts based on noble metals. The selection of the type of catalyst to be used consequently depends on the particular charge to be hydrogenated. A more detailed description of the hydrogenation of olefins is provided, for example, by F. Asinger, in "Mono-olefins: Chemistry and Technology", Pergamon Press, Oxford, page 455.

In the case of mixtures deriving from the dimerization of isobutene, whose average composition is the following:

| | |
|---|---|
| $C_8$ | 80-95% by weight |
| $C_{12}$ | 5-20% by weight |
| $C_{16}$ | 0.1-2% by weight | hydrogenation is not however an easy operation as:
the hydrogenation rate is inversely proportional to the chain length; the hydrogenation of $C_8$ olefinic dimers, in fact, requires a much lower temperature (60-100° C.) than that necessary for the hydrogenation of $C_{12}$ olefins (100-200° C.).

the most common hydrogenation catalysts (based on nickel or palladium) tend to become rapidly deactivated due to various poisons and in particular sulfurated compounds.

The presence of sulfur, which is practically inevitable in this type of charge, is the factor which, more than anything else, conditions the whole hydrogenation section.

Charges from FCC and coking are those which have the highest sulfur content (even up to 1000 ppm can be reached in the product) and they are therefore those which create the greatest problems in hydrogenation.

Lower quantities of sulfur, but which are still capable of reducing the competitiveness of conventional catalysts, can also be found in charges from Steam-Cracking and dehydrogenation processes of isobutane (in this case, the sulfurated compounds are charged into the dehydrogenation reactor to limit cracking reactions).

On the basis of these considerations, nickel catalysts, which are more economic, are therefore practically unusable (the sulfur content of the dimerization products is almost always higher than 1 ppm) whereas those based on supported noble metals can only be used under particular conditions (charges deriving from Steam-Cracking or from dehydrogenation processes of isobutane). In the case of charges from FCC, resort must be made to bimetallic catalysts such as those used in hydrotreating reactions, for example Ni/Co and/or Ni/Mo. These catalysts are insensitive to sulfurated compounds but are not very active; it is therefore necessary to use much more drastic operating conditions with respect to traditional hydrogenation catalysts (P 4-7 MPa and T 200-300° C.) which make the hydrogenation section extremely onerous.

SUMMARY OF THE INVENTION

It has been surprisingly found that, by distilling the dimerization product of isobutene, the sulfurated compounds (and poisons in general) tend for the most part to accumulate at the bottom of the column, whereas a stream consisting of $C_8$ olefins with a minimum sulfur content, is recovered at the head.

The process, object of the present invention, for the production of high-octane hydrocarbons starting from streams containing olefinic cuts and sulfurated compounds, obtained by the dimerization of isobutene, by means of hydrogenation, is characterized by fractionating said streams in one or more distillation columns in order to obtain two or more streams, with varying sulfur contents, containing said olefinic cuts and hydrogenating said streams separately.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
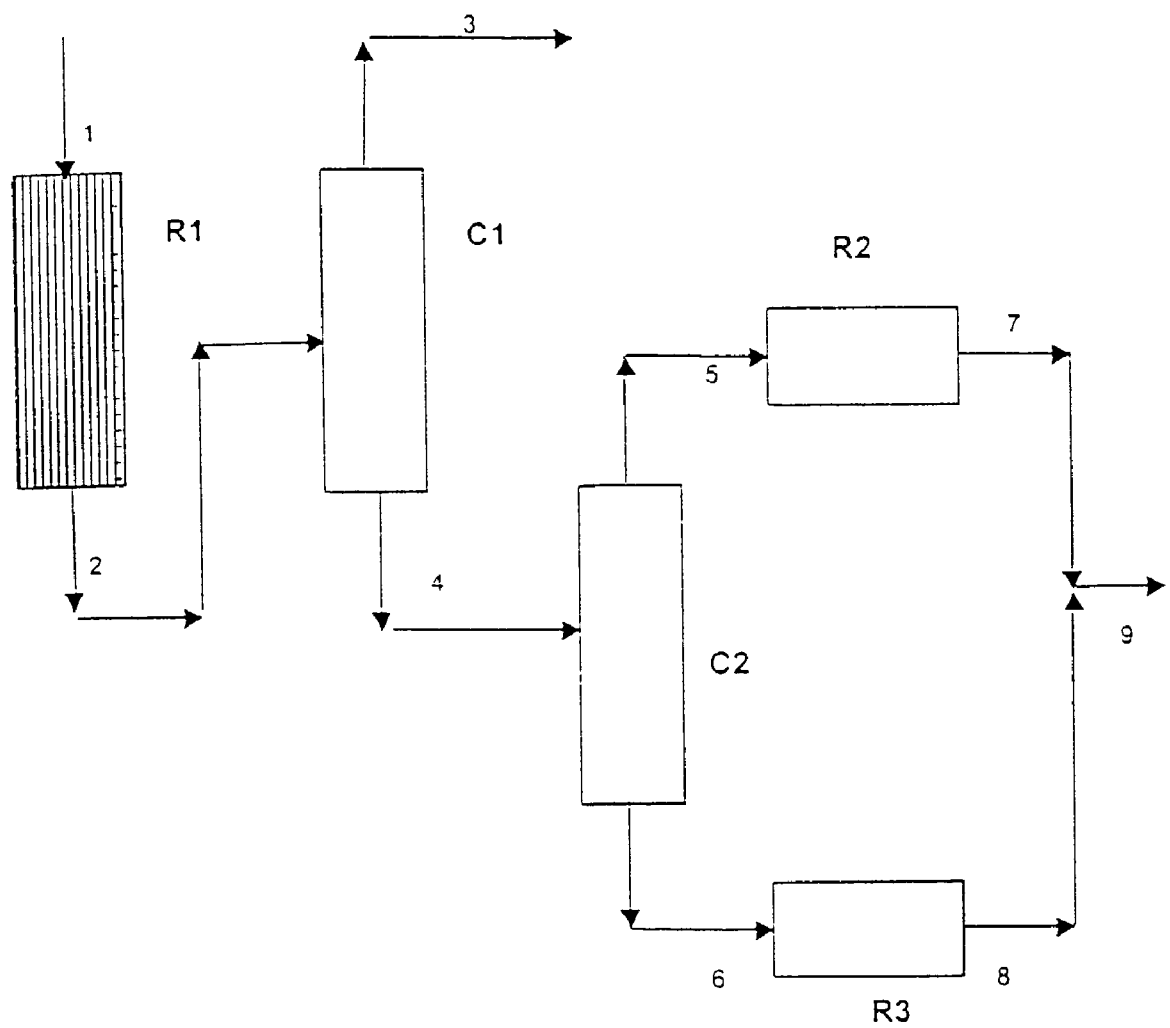
FIG. 1 is a schematic depiction of an exemplary plant scheme according to the present invention.

The two streams thus obtained can be hydrogenated separately as follows:

the head of the column, rich in $C_8$ olefins, which forms 60-90% of the stream, can be hydrogenated with conventional catalysts and bland operating conditions (lower temperatures and higher space velocities) with respect to the reaction conditions required for the hydrogenation of the whole fraction;

the bottom of the column, which forms 10-40% of the stream, can be hydrogenated with catalysts of the hydrotreating type.

The application of the present invention consequently has the advantage of making the hydrogenation step of $C_8$-$C_{16}$ olefinic streams for the production of high-octane compounds to be used as fuel components, technically easier and economically more attractive. In this case, in fact, it is not necessary to use extremely drastic conditions for hydrogenating the whole fraction (necessity of pre-heating the charge and using high quantities of hydrogen at high pressure) but on the contrary, most of the feeding is hydrogenated under very bland conditions with conventional catalysts.

The more drastic conditions are therefore only applied on a minor stream thus improving the economic aspect of the process. The present invention provides process flexibility allowing the problem of eliminating the sulfurated compounds to be kept separate from that relating to the hydrogenation of olefins, thus allowing refiners (but potentially any type of manufacturer) to choose the most convenient method.

More specifically, the process according to the invention can comprise the following steps:

a) dimerizing the isobutene contained in a $C_4$ cut (FCC, Coking, Steam-Cracking, Dehydrogenation of isobutane);

b) sending the product leaving the dimerization reactor to a first distillation column from whose head the $C_4$ products are recovered, whereas the $C_8$-$C_{16}$ mixture is recovered from the bottom;

c) sending the effluent from the bottom of the first column to a second distillation column from whose head pure $C_8$ olefins with a small quantity of sulfur are recovered, whereas most of the sulfur and contaminants are concentrated in the stream at the bottom;

d) hydrogenating the stream containing the $C_8$ olefins with commercial catalysts based on nickel or noble metals (for example palladium and/or platinum);

e) hydrogenating the stream at the bottom of the column rich in sulfur with sulfur-resistant catalysts such as bimetallic hydrotreating catalysts of the Ni/Mo and/or Ni/Co type;

f) optionally joining the two hydrogenated fractions so as to have a high-octane component, substantially sulfur-free, for fuels.

Alternatively, a process can be used, again according to the present invention, comprising the following steps:

a) dimerizing the isobutene contained in a $C_4$ cut (FCC, Coking, Steam-Cracking, Dehydrogenation of isobutane);

b) sending the product leaving the dimerization reactor to a single distillation column from whose head the $C_4$ products are recovered, and from whose bottom the $C_8$-$C_{16}$ mixture containing most of the sulfurated compounds, is recovered, the practically sulfur-free $C_8$ olefins, on the other hand, being removed, in liquid or vapour phase, as lateral cut of the column;

c) hydrogenating the stream containing the $C_8$ olefins with commercial catalysts based on nickel or noble metals (for example palladium and/or platinum);

d) hydrogenating the stream at the bottom of the column rich in sulfur with sulfur-resistant catalysts such as bimetallic hydrotreating catalysts of the Ni/Mo and/or Ni/Co type;

e) optionally joining the two hydrogenated fractions so as to have a high-octane component, substantially sulfur-free, for fuels.

The relative ratio between the quantity of fraction removed at the head with respect to that at the outlet of the bottom of the distillation column depends on the type of $C_4$ stream used as charge for the dimerization.

In the case of charges from Steam-Cracking and Dehydrogenation processes of isobutane, it is possible, on the basis of the low sulfur content, to further force the separation so that the fraction at the head represents 70-90% of the whole stream. In the case of charges from FCC and Coking, due to their high sulfur content, a smaller fraction (60-80% of the total) must be recovered at the head to maintain a sulfur level of less than 10 ppm.

A simplified process scheme is provided in FIG. 1 enclosed, to illustrate the present invention in more detail.

The stream (1) containing isobutene, for example deriving from Steam-Cracking or Coking or FCC or isobutane Dehydrogenation units, is sent to the reactor (R1) in which the isobutene is selectively converted to dimers.

The effluent (2) from the reactor is sent to a separation column (C1) from whose head a stream (3) is removed, essentially containing non-converted isobutene, linear olefins and saturated $C_4$ products (n-butane and isobutane), whereas a stream (4) consisting of dimers and higher oligomers is removed from the bottom.

This stream (4) is sent to a new distillation column (C2) from whose head a fraction (5) is recovered, consisting of $C_8$ olefins, which forms 60-90% of the feeding, whereas a stream (6) rich in $C_{12}$ olefins containing most of the sulfur is obtained at the bottom.

The stream (5) which has a very low sulfur content (<10 ppm), is sent to the reactor (R2) in which it is hydrogenated with conventional catalysts based on nickel or palladium and/or platinum (depending on the sulfur content in the charge). In this case, the hydrogenation is carried out on the light part of the charge ($C_8$ olefins) and therefore requires much less severe operating conditions than those necessary for treating the whole charge.

The stream at the bottom (6), on the other hand, is sent to another hydrogenation reactor (R3) having much smaller dimensions with respect to R2 as it must treat a smaller quantity of charge (10-40% of the total). In this stream, most of the sulfur present in the original charge is concentrated and consequently bimetallic catalysts (of the Ni/Co or Ni/Mo type), which require very drastic operating conditions but which, at the same time, are extremely sulfur-resistant, must be used for the hydrogenation.

The two hydrogenated streams (7) and (8) can be subsequently joined to obtain a saturated high-octane product (9) to be used as fuel component.

Figure 2:
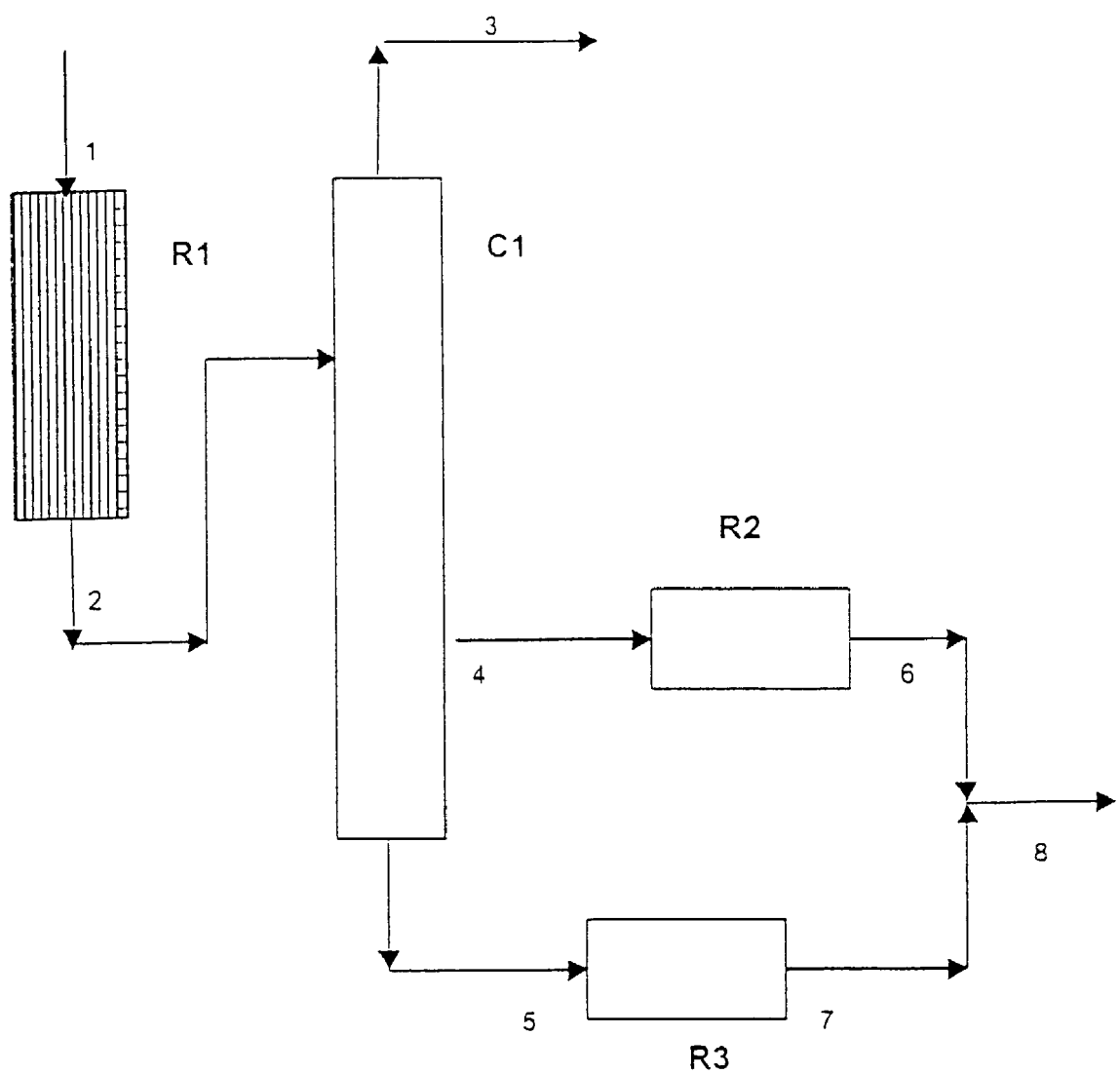
FIG. 2 is a schematic depiction of a further exemplary plant scheme according to the present invention.

Another possible plant configuration is illustrated in FIG. 2. In this case, the effluent of the reactor (2) is sent to a single distillation column (C1) from whose head a stream (3) is removed, essentially containing non-converted isobutene, linear olefins and saturated $C_4$ products (n-butane and isobutane), whereas the stream (5) containing most of the sulfur and mainly consisting of $C_{12}$ olefins, is removed from the bottom. The stream consisting of $C_8$ olefins (4), on the other hand, is removed as lateral cut (vapour and/or liquid phase).

The two streams (4) and (5) are then hydrogenated in two reactors (R2) and (R3) under the same conditions indicated above. The two hydrogenated streams (6) and (7) are subsequently joined to obtain a high-octane saturated product (8) to be used as fuel component.

The optimum cut ranges starting from the various streams are indicated below: if the olefinic cut has been produced starting from an FCC or Coking charge, the fraction at the head of the distillation column represents 60-80% of the whole stream, if the olefinic cut has been produced starting from a charge from Steam-Cracking or the Dehydrogenation of isobutane, the fraction at the head of the distillation column represents 70-90% of the whole stream.

A wide range of operating conditions can be used for the hydrogenation of olefins; it is possible to operate in vapour phase or liquid phase but the operating conditions in liquid phase are preferred.

The hydrogen pressure is preferably below 5 MPa, more preferably between 1 and 3 MPa. The reaction temperature preferably ranges from 30 to 200° C. The feeding space velocities of the olefinic streams are preferably lower than 20 $h^{-1}$, more preferably from 0.2 to 10 $h^{-1}$. The heat produced in the reaction is generally controlled by diluting the charge with a hydrogenated stream in a ratio lower than 20 (volume of saturated product/volume of olefin) and preferably ranging from 5 to 10.

Some examples are provided for a better illustration of the present invention but do not limit its scope in any way.

EXAMPLE 1

This example illustrates the use of the process of the present invention. A hydrocarbon fraction, obtained by the selective dimerization of isobutene contained in a stream from FCC, having the following composition:

| | |
|---|---|
| $C_8$ olefins | 89.7% by weight |
| $C_{12}$ olefins | 9.7% by weight |
| $C_{16}$ olefins | 0.6% by weight |
| Total sulfur | 50 ppm | was separated in a glass distillation column with 50 plates at atmospheric pressure so as to have a temperature of 108° C. at the head.

In this case, as the charge is quite rich in sulfur, the $C_8$-$C_{12}$ separation must be limited and only 70% of the feeding stream removed from the head of the column in order to have two fractions with the following characteristics:

| | Column head | Column bottom |
|---|---|---|
| fraction % | 70 | 30 |
| Sulfur, ppm | 6 | 151 |

The fraction at the head, with only 6 ppm of sulfur, was hydrogenated with a commercial palladium catalyst on alumina (0.5% by weight). Operating in liquid phase at 100° C., with a space velocity of 3 $h^{-1}$ (olefin volume over catalyst volume per hour) and a hydrogen pressure of 2 MPa, a conversion of olefins of over 99.9% was obtained.

The stream at the bottom, on the other hand, was hydrogenated with a catalyst based on Ni/Mo operating under much more drastic conditions, with temperatures of 280° C., hydrogen pressures of 5 MPa, and space velocities of 1 $h^{-1}$; under these conditions a conversion of olefins of 97% was obtained.

On joining the two fractions, a high-octane product was obtained with a content of residual olefins of less than 1% and less than 2 ppm of sulfur.

EXAMPLE 2

This example deals with the hydrogenation of a $C_8$-$C_{12}$ olefinic mixture, obtained by the dimerization of isobutene contained in a stream leaving a dehydrogenation plant of isobutane, having the following characteristics:

| | |
|---|---|
| $C_8$ olefins | 86.5% by weight |
| $C_{12}$ olefins | 12.8% by weight |
| $C_{16}$ olefins | 0.7% by weight |
| Total sulfur | 10 ppm |

This sulfur value represents the maximum limit tolerated by traditional hydrogenation catalysts and it is therefore convenient to effect a separation.

Due to the low sulfur content of the fraction, it was possible to further force the separation in the column, so as to have a temperature at the head of 112° C., and obtain a fraction which is 80% of the total fed.

| | Column head | Column bottom |
|---|---|---|
| fraction % | 80 | 20 |
| Sulfur, ppm | 1 | 30 |

The stream at the head, with only one ppm of sulfur, was hydrogenated with a commercial catalyst based on nickel.

Operating in liquid phase at 100° C., with a space velocity of 3 $h^{-1}$ (olefin volume over catalyst volume per hour) and a hydrogen pressure of 2 MPa, a conversion of the olefins of over 99.9% was obtained.

The stream at the bottom, on the other hand, was hydrogenated with a catalyst based on Ni/Mo operating under much more drastic conditions, with temperatures of 280° C., hydrogen pressures of 5 MPa, and space velocities of 1 $h^{-1}$; under these conditions a conversion of olefins of 97% was obtained.

On joining the two fractions, a high-octane product was obtained with a content of residual olefins of less than 1% and less than 1 ppm of sulfur.

The invention claimed is:

1. A process for the production of high-octane hydrocarbons, which comprises:
    a) dimerizing isobutene that is present in a $C_4$ cut of a hydrocarbon stream in a dimerization reactor;
    b) distilling said hydrocarbon stream containing dimerized isobutene in a first distillation column from whose head $C_4$ products are recovered and from the bottom of which a $C_8$-$C_{16}$ mixture is recovered as an effluent;
    c) distilling said effluent in a second distillation column from whose head pure $C_8$ olefins with a small quantity of sulfur are recovered and from whose bottom a stream comprising most of the sulfur and concentrated contaminants is obtained;
    d) hydrogenating the stream containing the $C_8$ olefins with a nickel or a noble metal based catalyst;

e) hydrogenating said stream rich in sulfur over a sulfur resistant catalyst comprising a Ni/Mo and/or a Ni/Co catalyst; and f) optionally combining the two hydrogenation fractions so as to prepare a high-octane component, substantially sulfur-free, for fuels.

2. The process according to claim 1, wherein the noble metal hydrogenation catalyst of step (d) is a palladium and/or platinum catalyst.

3. The process according to claim 1, wherein said head fraction of step (c) ranges in amount from 60 to 90% by weight of the entire hydrocarbon stream containing olefinic cuts that is processed to a fuel component.

4. The process according to claim 1, wherein, when the $C_4$ cut has been produced starting from an FCC or coking charge, said head fraction of step (c) ranges in amount from 60 to 80% by weight of the entire hydrocarbon stream that enters the second distillation column.

5. The process according to claim 1, wherein, when the $C_4$ cut has been produced starting from a charge from Steam-Cracking or the Dehydrogenation of isobutane, said head fraction of step (c) ranges in amount from 70 to 90% by weight of the entire hydrocarbon stream that enters the second distillation column.

6. The process according to claim 1, wherein the head, fraction of step (c) is hydrogenated over a nickel or noble metal hydrogenation catalyst at a space velocity (olefin volume over catalyst volume per hour) ranging from 0.1 to 10 $h^{-1}$.

7. The process according to claim 6, wherein said space velocity ranges from 2 to 4 $h^{-1}$.

8. The process according to claim 1, wherein the olefinic cut to be hydrogenated consists of $C_8$-$C_{16}$ olefins, whose $C_{12}$ olefins content ranges from 5 to 20% by weight of the $C_8$-$C_{16}$ olefins, whereas the $C_{16}$ olefins content ranges from 0.5 to 2% by weight of the $C_8$-$C_{16}$ olefins.

9. A process for the production of high-octane hydrocarbons, which comprises:

a) dimerizing isobutene that is present in a $C_4$ cut of a hydrocarbon stream in a dimerization reactor;

b) distilling said hydrocarbon stream containing dimerized isobutene in a single distillation column from whose head $C_4$ products are recovered and from whose bottom a $C_8$-$C_{16}$ mixture containing sulfurated compounds is recovered, and a lateral cut being obtained as a liquid or vapor that is comprised of essentially sulfur free $C_8$ olefins;

c) hydrogenating the stream of the lateral cut containing $C_8$ olefins over a nickel or noble metal catalyst;

d) hydrogenating the stream that is rich in sulfur obtained from the bottom of the distillation column over a sulfur resistant catalyst comprising a Ni/Mo and/or a Ni/Co catalyst; and e) optionally combining the two hydrogenation fractions so as to prepare a high-octane component, substantially sulfur-free, for fuels.

10. The process according to claim 9, wherein the noble metal hydrogenation catalyst of step (c) is a palladium and/or platinum catalyst.

11. The process according to claim 9, wherein said lateral cut ranges in amount from 60 to 90% by weight of the entire hydrocarbon stream containing olefinic cuts that is processed to a fuel component.

12. The process according to claim 9, wherein, when the $C_4$ cut has been produced starting from an FCC or coking charge, the lateral cut of step (b) ranges in amount from 60 to 80% by weight of the entire hydrocarbon stream that enters said single distillation column.

13. The process according to claim 9, wherein, when the $C_4$ cut has been produced starting from a charge from Steam-Cracking or the Dehydrogenation of isobutane, the lateral cut of step (b) ranges in amount from 70 to 90% by weight of the entire hydrocarbon stream that enters said single distillation column.

14. The process according to claim 9, wherein said lateral cut comprised of essentially sulfur free $C_8$ olefins, is hydrogenated over a nickel or noble metal hydrogenation catalyst at a space velocity (olefin volume over catalyst volume per hour) ranging from 0.1 to 10 $h^{-1}$.

15. The process according to claim 14, wherein said space velocity ranges from 2 to 4 $h^{-1}$.

16. The process according to claim 9, wherein the olefinic cut to be hydrogenated consists of $C_8$-$C_{16}$ olefins, whose $C_{12}$ olefins content ranges from 5 to 20% by weight of the $C_8$-$C_{16}$ olefins, whereas the $C_{16}$ olefins content ranges from 0.5 to 2% by weight of the $C_8$-$C_{16}$ olefins.

* * * * *